United States Patent [19]

Mühlbauer

[11] Patent Number: 4,732,302
[45] Date of Patent: Mar. 22, 1988

[54] DEVICE FOR THE METERED DISCHARGE OF DENTAL MATERIAL

[76] Inventor: Ernst Mühlbauer, Fangdieckstrasse 61, 2000 Hamburg 53, Fed. Rep. of Germany

[21] Appl. No.: 869,219

[22] Filed: Jun. 2, 1986

[30] Foreign Application Priority Data

Jul. 25, 1985 [DE] Fed. Rep. of Germany ... 8521514[U]

[51] Int. Cl.⁴ .............................................. A61C 5/04
[52] U.S. Cl. .................... 222/390; 222/470; 433/90; 604/224; 604/227
[58] Field of Search ............... 222/390, 465 R, 470, 222/471, 191; 604/224, 227; 433/89, 90, 81

[56] References Cited

U.S. PATENT DOCUMENTS

| 913,297 | 2/1909 | Krautschneider | 222/95 X |
|---|---|---|---|
| 1,235,134 | 7/1917 | Gordon | 222/390 X |
| 1,259,474 | 3/1918 | Barr | 222/390 X |
| 2,888,923 | 6/1959 | Cunha Reis | 604/224 X |
| 3,212,685 | 10/1965 | Swan et al. | 222/390 X |
| 4,189,065 | 2/1980 | Herold | 222/390 X |
| 4,479,781 | 10/1984 | Herold et al. | 222/390 X |
| 4,560,352 | 12/1985 | Neümeister et al. | 222/390 X |

FOREIGN PATENT DOCUMENTS

| 2741185 | 2/1979 | Fed. Rep. of Germany . |
| 3129348 | 2/1983 | Fed. Rep. of Germany . |
| 2347856 | 11/1977 | France . |
| 7629377 | 11/1977 | France . |

Primary Examiner—L. J. Paperner
Assistant Examiner—P. McCoy Smith
Attorney, Agent, or Firm—Chilton, Alix & Van Kirk

[57] ABSTRACT

A cartridge (1) contains dental material and at one end has a discharge nozzle (2) and at the other end is connected fixedly in terms of rotation to a nut (3) having an internal thread. A plunger is disposed at the end of a spindle (4) in the cartridge, for ejecting the dental material from the nozzle (2). A handle (6) is connected fixedly in terms of rotation to the spindle. The handle (6) and grip part (8) thereof are grasped in the lower portion of the hand, while the thumb and forefinger rotate the cartridge relative to the spindle to discharge the material.

7 Claims, 3 Drawing Figures

U.S. Patent | Mar. 22, 1988 | 4,732,302
Fig.1
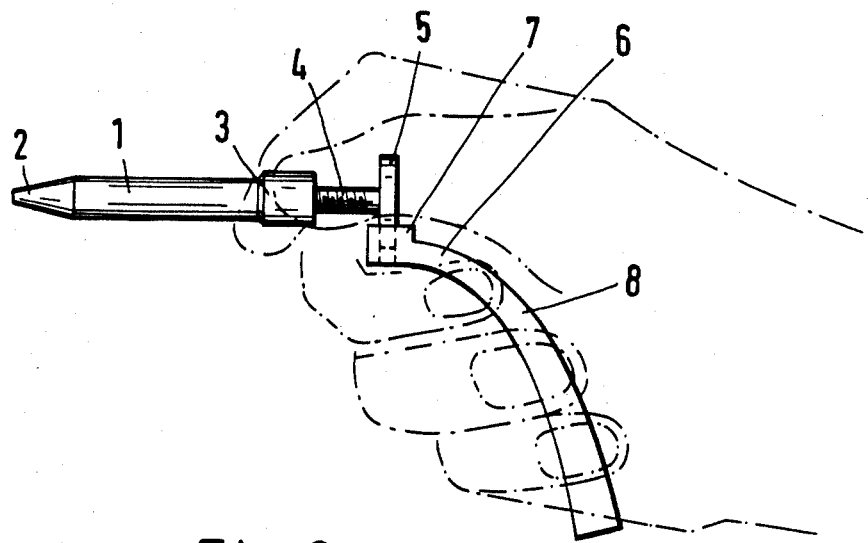
Fig.2
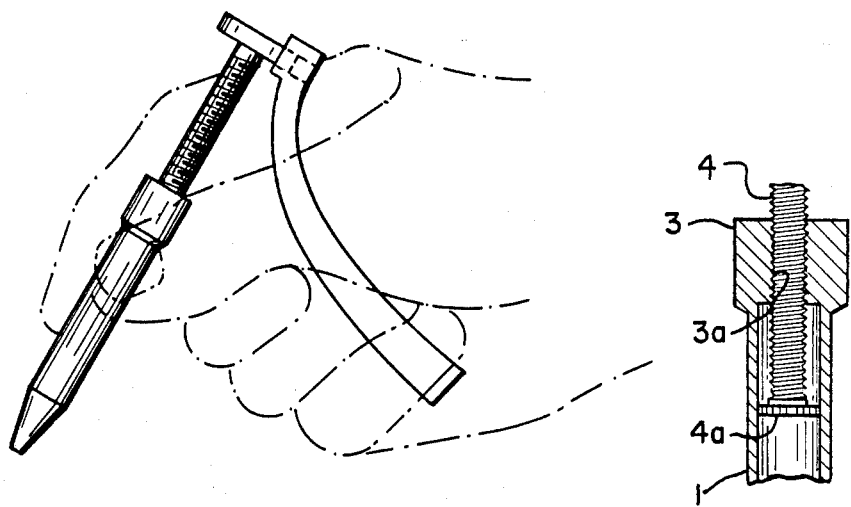
Fig. 3

DEVICE FOR THE METERED DISCHARGE OF DENTAL MATERIAL

DESCRIPTION

The invention relates to a device for the metered and aimed discharge of dental material with a cartridge which contains the dental material and which at one end has a discharge nozzle and at the other end is connected fixedly in terms of rotation to a nut having an internal thread, with a plunger in the cartridge for ejecting the dental material from the nozzle, with a threaded spindle interacting with the nut and advancing the plunger as a result of the relative rotation of the cartridge and the spindle, and with a handle connected fixedly in terms of rotation to the spindle.

In a known device (German patent specification No. 2,741,185), the nut is arranged rotatably on the rear end of the cartridge and the cartridge has a flange in front of the nut, so that the instrument can be held between the index and middle fingers grasping the cartridge in front of the flange, on the one hand, and the ball of the thumb, against which the handle of the spindle is pressed by the said fingers, the thumb remaining free to rotate the nut. During use, the cartridge and the spindle are held firmly without rotation; only the nut is rotated. It is necessary for the cartridge to be in a stationary position, because the discharge nozzle is attached to it in a curve. The construction of this known appliance involves a very high outlay. There is also a disadvantage in its use, because only the thumb is available for the rotary movement, and this rests against the nut under lateral pressure and therefore makes it difficult to aim the discharge nozzle.

In another known appliance (DE-A No. 3,212,187=U.S. Pat. No. 4,479,781, the nut is connected firmly to the cartridge, and the nozzle is arranged coaxially relative to the cartridge. The handle is connected, on the one hand, to the housing rotatably, but fixedly in the axial direction and, on the other hand, to the spindle non-rotatably, but so as to be displaceable in the axial direction. While the instrument can be held by the handle between the middle finger, ring finger, small finger and ball of the thumb, the cartridge can be rotated by means of the thumb and index finger to discharge the material. It is not at all simple in construction terms to connect the handle to the housing fixedly in the axial direction, but rotatably and, on the other hand, to the spindle non-rotatably, but so as to be displaceable in the axial direction. The constructional idea already explained consequently had to be modified (DE-A No. 3,240,785=U.S. Pat. No. 4,560,352), so that as a result the overall design becomes relatively complicated.

A dispensing syringe for dental purposes is also known, its plunger being connected firmly to a threaded spindle which itself can be advanced by means of a nut provided rotatably on the rear end of the cylinder. This syringe can only be used with two hands, because the syringe body cannot be held and the nut rotated at the same time with one and the same hand No. (DE-A- 3,129,348).

Finally, a syringe for discharging any plastic materials without particular reference to dental use is known, and in this the spindle provided for advancing the plunger in the syringe cylinder is guided through a nut provided fixedly in terms of rotation on the rear end of the syringe body and at the end has a handle. To discharge the material, the syringe cylinder can be held with one hand, while the handle on the spindle is rotated with the other hand No. (FR-U-2,347,856). There is no question of one-handed operation; nor is this possible, because the syringe illustrated, by its very nature, is too large to be held and operated in one hand.

The object on which the invention is based is, therefore, to provide a device of the type mentioned in the introduction, which has a very simple design, but which can be handled easily.

In the solution according to the invention, the handle is connected fixedly solely to the spindle, specifically, not only fixedly in terms of rotation, but also fixedly in the axial direction, the discharge nozzle being arranged coaxially relative to the internal thread of the nut, and the handle has a grip part projecting laterally from the cartridge in the manner of a pistol grip.

Surprisingly, it has been shown that the cartridge is held sufficiently securely by the spindle, even when the handle is connected solely to the spindle and cannot exert any direct holding forces on the cartridge. It is also surprising that the change in distance, occurring when the spindle is progressively screwed into the cartridge, does not have an adverse effect on the handling. This is because the difference in distance is relatively slight in comparison with the differences in position, to which a hand practised in the use of different instruments is accustomed in any case.

This results in an instrument which outwardly consists of only the cartridge, spindle and handle, and in which no sliding or rotary connections between the handle and another part of the instrument have to be provided. On the contrary, a simple, firm, albeit appropriately releasable connection between the handle and the spindle is sufficient.

The spindle preferably has a first transversely directed plug-connection element which can be connected firmly to a second plug-connection element provided fixedly on the handle. In this case, the grip part of the handle extends in a direction different from the direction of the longitudinal axis of the second plug-connection element. The two plug-connection elements can be joined together in two positions. In the first of these positions, the grip part of the handle extends essentially to the side of the spindle, whilst in the other of the two positions it is placed essentially behind the spindle. The user is therefore free to attach the handle to the rest of the device in the way which seems most convenient to him for handling. As long as the cartridge is still full and the spindle therefore projects beyond the cartridge far to the rear, it is often expedient to attach the handle in the position in which it is located essentially to the side of the spindle, whereas, when the cartridge is almost empty and the spindle therefore only projects beyond the cartridge a little way at the rear, the other position, which is also suitable for larger hands, is recommended.

The length of the handle will not be less than the length of the cartridge. It will preferably be somewhat greater.

The invention is explained in detail below with reference to the drawing which illustrates an advantageous exemplary embodiment diagrammatically in side views. In the drawing:

FIG. 1 shows the arrangement with the handle in the rear insertion position, and FIG. 2 shows the arrangement with the handle in the front insertion position.

FIG. 3 is a longitudinal section view of the interaction of the threaded nut portion of the cartridge with the threaded spindle.

The cartridge (1) carries at its front end the discharge nozzle (2) and at its rear end the nut (3) which is connected fixedly to the remaining cartridge body and has an internal thread 3a, and in which the spindle (4) can be screwed, in order to advance inside the cartridge (1) a plunger 4a and thereby squeeze the dental material out of the nozzle (2). The spindle (4) carries, at its rear end, a first plug-connection element (5) in the form of a crossbar of square cross-section, which can also be used as such to screw in the spindle (4), although this requires the use of two hands. The handle (6) is fastened releasably to one end of the first plug-connection element (5). At its end, it has as a second plug-connection element a socket (7) which has a square bore matching the cross-section of the first plug-connection element and which is simply attached onto one of its ends. Of course, any other type of releasable connection between the handle (6) and the spindle (5) can be used.

The handle (6) is bent slightly, so that the main direction of its grip part (8) differs from the direction of the plug element (5). It projects from the cartridge (1), for example in the manner of a pistol grip.

The handle (6), when in the position according to FIG. 1, is used when the user has a large hand or when the spindle (4) is already screwed far into the cartridge (1), or when the particular desirable position of the cartridge in relation to the hand makes this seem appropriate. Instead, in exceptional cases, the position according to FIG. 2 can also be selected if the user has a small hand or the spindle still projects a long way from the cartridge, or if it is desirable to adopt a particular position of use of the cartridge in relation to the direction of the hand.

The instrument is grasped in the way indicated approximately by dot-and-dash lines, the handle (6) being held by the middle finger, ring finger and small finger, whilst the index finger and thumb are available for rotating the cartridge (1) or the nut (3) and at the same time can easily aim the instrument.

I claim:

1. A device for the metered and aimed discharge of dental material comprising: a cartridge for containing the dental material and which at one end has a discharge nozzle and at the other end is connected fixedly in terms of rotation to a nut having an internal thread, the discharge nozzle being arranged coaxially relative to the internal thread of the nut; a plunger in the cartridge for ejecting the dental material from the nozzle; a threaded spindle interacting with the nut to advance the plunger as a result of the rotation of the cartridge around the spindle; a handle connected solely to the spindle, the handle having a grip part projecting laterally relative to the cartridge in the manner of a pistol grip; wherein the handle, the connection of the handle to the spindle and the nut are arranged to be grasped simultaneously in one hand such that the index finger and thumb can rotate the nut and cartridge while the handle and spindle remain stationary, thereby advancing the cartridge axially relative to the plunger to discharge the dental material through the nozzle.

2. A device as claimed in claim 1, wherein the handle (6) is connected releasably to the spindle (4).

3. A device as claimed in claim 1, wherein the spindle has a first transversely directed plug-connection element (5) which is connectable to a second plug-connection element (7) fixed up the handle, wherein the grip part (8) of the handle extends in a direction different from the direction of the longitudinal axis of the second plug-connection element (7), and wherein the second plug-connection element (7) can be attached on the first plug-connection element (5) in two positions, the grip part (8), in one of these positions, being placed essentially to the side of the spindle (4) and, in the other position, being placed essentially behind the spindle (4).

4. A device as claimed in claim 1, wherein the length of the grip part (8) is at least approximately equal to the length of the cartridge (1).

5. A device as claimed in claim 2, wherein the spindle has a first transversely directed plug-connection element (5) which is connectable to a second plug-connection element (7) fixed to the handle, wherein the grip part (8) of the handle extends in a direction different from the direction of the longitudinal axis of the second plug-connection element (7), and wherein the second plug-connection (7) can be attached on the first plug-connection (5) in two positions, the grip part (8), in one of these positions, being placed essentially to the side of the spindle (4) and, in the other position, being placed essentially behind the spindle (4).

6. A device as claimed in claim 2, wherein the length of the grip part (8) is at least approximately equal to the length of the cartridge (1).

7. A device as claimed in claim 3, wherein the length of the grip part (8) is at least approximately equal to the length of the cartridge (1).

* * * * *

UNITED STATES PATENT AND TRADEMARK OFFICE
CERTIFICATE OF CORRECTION

PATENT NO. : 4,732,302
DATED : March 22, 1988
INVENTOR(S) : Ernst Muhlbauer

It is certified that error appears in the above-identified patent and that said Letters Patent is hereby corrected as shown below:

Column 4, line 4 of claim 3, "up" should be --to-- .

Signed and Sealed this

Eighth Day of September, 1992

Attest:

DOUGLAS B. COMER

*Attesting Officer*   Acting Commissioner of Patents and Trademarks